US00PP20864P2

(12) United States Plant Patent
Bradford

(10) Patent No.: US PP20,864 P2
(45) Date of Patent: Mar. 23, 2010

(54) INTERSPECIFIC TREE NAME 'PLUMRED III'

(50) Latin Name: ***Prunus* sp.**
Varietal Denomination: Plumred III

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/316,595

(22) Filed: Dec. 15, 2008

(51) Int. Cl.
*A01H 5/00* (2006.01)

(52) U.S. Cl. ..... Plt./180

(58) Field of Classification Search ..... Plt./180, Plt./184, 186
See application file for complete search history.

(56) References Cited

U.S. PATENT DOCUMENTS

PP7,503 P 4/1991 Bradford
PP13,478 P2 1/2003 Bradford

*Primary Examiner*—June Hwu

(57) ABSTRACT

The present invention relates to an interspecific tree and more particularly to a new and distinct variety broadly characterized by a medium size, moderately vigorous, hardy, and productive tree. Being self-unfruitful, the present variety requires cross pollination from an apricot, interspecific, or plum that blooms during the mid season. The fruit matures under the ecological conditions described during the latter half of June, with first picking on Jun. 20, 2008. The fruit is uniformly large in size, very dark red in skin color, semi-freestone in type, oblate in shape, red in flesh color, firm in texture, and sweetly acidic in flavor.

1 Drawing Sheet

Botanical classification: *Prunus* sp.

Varietal denomination: 'PLUMRED III'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumred III'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing 'Purple Majesty' plum (U.S. Plant Pat. No. 7,503) was crossed by me in this manner. To pollinate this plum, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H1 15P". They were grown as seedlings on their own root in my greenhouse and upon reaching dormancy transplanted to a cultivated area of my experimental orchard located near Le Grand, Calif. in Merced County (San Joaquin Valley). During the spring of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, 'Purple Majesty' plum by being self-unfruitful and by producing fruit that is dark red to purple in skin color, firm in texture, oblate in shape, and matures just past mid June, but is distinguished therefrom by producing fruit that is sweeter in flavor, much larger in size, semi-freestone instead of clingstone, and dark red in flesh color instead of orange yellow.

The present variety is similar to 'Yummybeaut' (U.S. Plant Pat. No. 13,478) plum by being self-unfruitful and by producing fruit that is dark red to purple in skin color, firm in texture, and matures in the second half of June, but is distinguished therefrom by having a more prolific bloom, by producing more pollen, and by producing fruit that is sweeter in flavor, much larger in size, semi-freestone instead of clingstone, oblate instead of globose in shape, and dark red in flesh color instead of yellow.

SUMMARY OF VARIETY

The present interspecific variety is characterized by a medium size, moderately vigorous, hardy, and productive tree. Being self-unfruitful, the present variety requires cross pollination from an apricot, interspecific, or plum that blooms during the mid season. The fruit matures under the ecological conditions described during the second half of June, with first picking on Jun. 20, 2008. The fruit is uniformly large in size, very dark red in skin color, semi-freestone in type, oblate in shape, red in flesh color, firm in texture, and sweetly acidic in flavor.

DRAWING

The accompanying photograph consists of four whole fruits positioned to display the characteristics of the skin color and form, one fruit divided around the suture to reveal the flesh and stone, a young tip shoot growth, typical leaves, and three insets depicting the flower buds and blossoms as they appeared during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Jun. 23, 2008, on the original tree during its seventh growing season. The flower and bud descriptions were developed during the previous blooming season. All major color code designations are by reference to the Inter-Society Color Council, National Bureau of Standards. Common color names are also used occasionally.

Parentage

Seed parent: 'Purple Majesty' plum (U.S. Plant Pat. No. 7,503).

Pollen parent: Unknown.

Tree

Size: Medium, reaching a height of 11' [3.35 m.] and a spread of 10' [3.05 m.] after seven growing seasons utilizing typical dormant pruning.

Vigor: Moderately vigorous, responding typically to irrigation and fertilization. The variety grows about 4' [1.22 m.] of surplus top-growth during the spring and summer. The plant should be grown on a standard commercial rootstock for production purposes.

Growth: Spreading and dense.

Form: Pruned to a central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid seasonal blooming apricot, interspecific, or plum, such as 'AUGUST YUMMY' (U.S. Plant Pat. No. 14,247).

Bearinq: Regular bearer, with no crop failures observed.

Trunk:

- *Size*.—Medium, reaching a maximum diameter of 5⅛" [130 mm.] after the seventh growing season.
- *Texture*.—Medium shaggy.
- *Bark color*.—A Dark grayish brown [62. d.gy.Br] and Grayish yellowish brown [80. gy.yBr] variegation with Light orange yellow [70. l.OY] crevices present.
- *Lenticels*.—Approximate Number Per Square Inch: 10. Color: Light orange yellow [70. l.OY]. Average Size: ⅜" [9.5 mm.]. Shape: Elongated, eye-shaped.

Branches:

- *Size*.—Diameter of the central leader is 2½" [63.5 mm.] measured 12" above the first lateral hanger, which itself has a maximum diameter of ⅞" [22.2 mm.].
- *Texture*.—Fairly smooth on first and second year wood; increasing roughness thereafter.
- *Color*.—1st Year Wood Topside: Moderate yellowish brown [77. m.yBr]. 1st Year Wood Underside: Strong yellow green [117. s.YG]. 2$^{nd}$ Year Wood: Deep brown [56. deep Br].
- *Lenticels*.—Number Per Square Inch: More than 50 on second year wood. Color: Light orange yellow [70. l.OY]. Average Size: 1/64" [0.4 mm.]. Shape: Elongated, eye-shaped.

Leaves:

- *Size*.—Medium. Average Length: 3 7/16" [87.3 mm.]. Average Width: 1⅞" [47.6 mm.].
- *Arrangement*.—Alternate.
- *Thickness*.—Medium.
- *Form*.—Elliptical.
- *Apex*.—Acuminate.
- *Base*.—Acute with an average angle base angle of 75 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: ½" [12.7 mm.]. Average Thickness: 1/16" [1.6 mm.]. Color: Light yellow green [119. l.YG] on the underside, Moderate reddish orange [37. m.rO] where more exposed to sunlight.
- *Stipules*.—Number: 2 per leaf at the young stage, up to 6 per growing tip. Average Length: 5/16" [7.9 mm.]. Color: Strong yellow green [117. s.YG] becoming Grayish reddish orange [39. gy.rO] with age.
- *Glands*.—Average Number: 3 per leaf. Position: Alternately and oppositely positioned at the intersection of the petiole and the leaf blade. Size: Small. Form: Globose. Color: Light yellow green [119. l.YG] acquiring a Moderate reddish brown [43. m.rBr] center with age. Leaf buds: Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, about thirty stamens, five sepals and petal locations alternately positioned.

- *Average flower diameter*.—1" [25.4 mm.].
- *Number of petals*.—Five, no double blossoms observed.
- *Petal shape*.—Oval to circular.
- *Petal margin*.—Entire, wavy.
- *Average petal diameter*.—7/16" [11.1 mm.].
- *Average petal length*.—½" [12.7 mm.].
- *Petal apex*.—Rounded.
- *Petal base*.—Obtuse.
- *Petal color*.—White [263. White] on both sides.
- *Anther color*.—Deep orange yellow [69. deep OY].
- *Stigma color*.—Light greenish yellow [101. l.gY].
- *Sepal color*.—Brilliant yellow green [116. brill.YG] on the outer surface.
- *Sepal length*.—5/32" [4.0 mm.].
- *Sepal width*.—5/32" [4.0 mm.].
- *Sepal apex*.—Rounded to elliptical to match the width and length.
- *Sepal margin*.—Fairly smooth, with slight serrations toward the apex.
- *Average pistil length*.—½" [12.7 mm.].
- *Average stamen length*.—⅜" [9.5 mm.].
- *Fragrance*.—Moderate.
- *Pollen production*.—Abundant, strong bee enticement.
- *Bloom density*.—Heavy.

*Number per cluster.*—2 to 7, average 3.
*Blooming period.*—Medium, three days before 'Santa Rosa' plum (unpatented).
*Onset of bloom.*—One percent on Feb. 24, 2008.
*Date of full bloom.*—Mar. 2, 2008.
*Duration of bloom.*—One to two weeks, dependent on ambient temperature.

Fruit

Maturity when described: Firm ripe, Jun. 23, 2008.
Date of first picking: Jun. 20, 2008.
Date of last picking: Jun. 30, 2008.
Size: Uniform, large.
*Average diameter axially.*—2½" [63.5 mm.].
*Average diameter across cheek plane.*—2¾" [69.9 mm.].
*Average diameter across suture plane.*—2 13/16" [71.5 mm.].
*Typical weight.*—6.4 ounces [181 grams].
Form: Oblate, slightly asymmetrically.
*Longitudinal section form.*—Oblate.
*Axial view.*—Round.
Suture: A shallow groove extending from the base just to the pistil point, somewhat sharper near the base.
Ventral surface: Rounded, very slight lipping.
Lips: Equal.
Cavity: Flaring, slightly elongated in the suture plane, suture showing on one side, some stem indentations present on the shoulders.
*Depth.*—⅜" [9.5 mm.].
*Breadth.*—15/16" [23.8 mm.].
Base: Truncate, slightly cordate if viewed parallel to the suture.
Apex: Mostly rounded to slightly truncate.
Pistil point: An inconspicuous dot at the end of the suture.
Stem: Medium.
*Average length.*—7/16" [11.1 mm.].
*Average width.*—3/32" [2.4 mm.].
Skin:
*Thickness.*—Medium.
*Surface.*—Smooth.
*Tenacity.*—Tenacious to the flesh.
*Astringency.*—Slight.
*Tendency to crack.*—Non observed in dry season.
*Color.*—Very deep red [17. v.d.R] over a Deep red [13. deep R] background with the slightest amount of Light yellowish brown [76. l.yBr] freckling toward the apex.
*Bloom.*—Abundant.
Flesh:
*Color.*—Very deep red [14. v.deep R] near the skin becoming Very red [11. v.R] in the center and toward the stone with Light orange yellow [70. l.OY] fibers emanating out from the stone.
*Surface of pit cavity.*—Covered with a mixture of Strong red [12. s.R] and Light orange yellow [70. l.OY] fibers.
*Amygdalin.*—Moderate.
*Juice.*—Abundant, rich.
*Texture.*—Firm, Tough, meaty.
*Fibers.*—Abundant, fine, tender.
*Ripens.*—Somewhat earliest at apex.
*Flavor.*—A tasty blend of acid and sugar, typically 19 brix.
*Aroma.*—Very slight.
*Eating quality.*—Outstanding.

Stone

Type: Semi-freestone.
Form: Oval.
Hilum: Narrow, oblong.
Base: Truncate.
Apex: Obtuse, with a sharp 3/32" [2.4 mm.] tip.
Sides: Equal.
Surface: Rough throughout with ridges on each side of the dorsal fin.
External color of stone: Deep orange yellow [69. deep OY] when first removed.
Pit wall color when cracked: Pale orange yellow [73. p.OY].
Cavity surface color: Dark orange yellow [72. d.OY].
Average pit wall thickness: 1/16" [1.6 mm.]
Average width: ⅝" [15.9 mm.].
Average length: ⅞" [22.2 mm.].
Average breadth: ⅜" [9.5 mm.].
Tendency to split: Slight.
Kernel:
*Form.*—Oval.
*Skin color.*—Moderate orange yellow [71. m.OY] becoming Brownish orange [54. brO] when dry.
*Pellicle color.*—Light grayish yellowish brown [79. l.gy.yBr].
*Vein color.*—Moderate brown [58. m.Br].
*Taste.*—Bitter.
*Viable.*—Yes.
*Average width.*—⅜" [9.5 mm.].
*Average length.*—½" [12.7 mm.].
*Amygdalin.*—Moderate.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'Yummybeaut' (U.S. Plant Pat. No. 13,478) plum by being self-unfruitful and by producing fruit that is dark red to purple in skin color, firm in texture, and matures in the second half of June, but is distinguished therefrom by having a more prolific bloom, by producing more pollen, and by producing fruit that is sweeter in flavor, much larger in size, semi-freestone instead of clingstone, oblate instead of globose in shape, and dark red in flesh color instead of yellow.

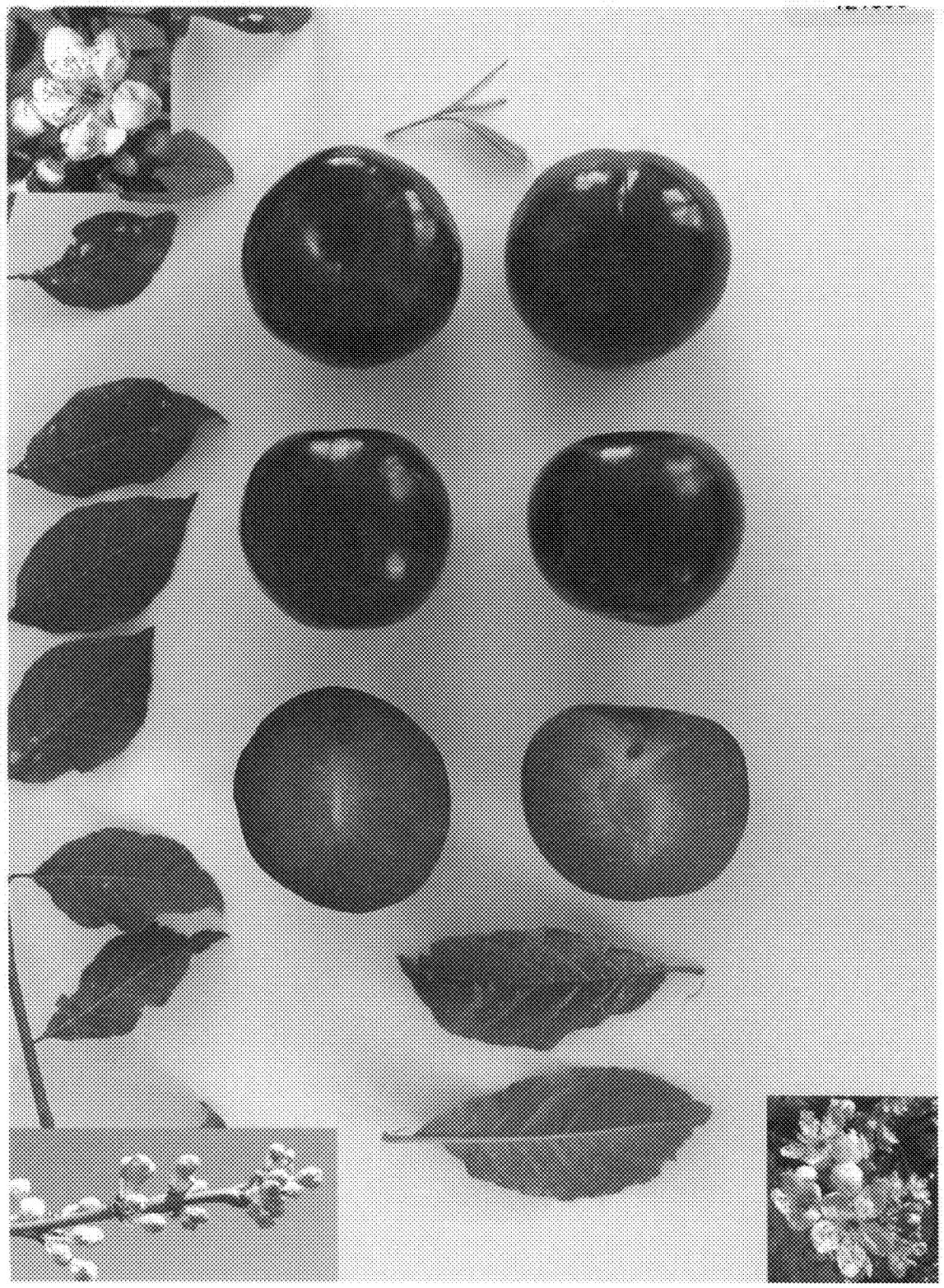

* * * * *